(12) United States Patent
Huang et al.

(10) Patent No.: US 12,343,118 B2
(45) Date of Patent: Jul. 1, 2025

(54) NEUROVASCULAR AGE PREDICTION SYSTEM BASED ON WHITE MATTER HYPERINTENSITY SIGNAL AND METHOD THEREOF

(71) Applicant: NATIONAL YANG MING CHIAO TUNG UNIVERSITY, Hsinchu (TW)

(72) Inventors: Chu-Chung Huang, Hsinchu (TW); Ching-Po Lin, Hsinchu (TW)

(73) Assignee: MiTech.ai Co., Ltd., Taipei (TW)

( * ) Notice: Subject to any disclaimer, the term of this patent is extended or adjusted under 35 U.S.C. 154(b) by 251 days.

(21) Appl. No.: 17/882,513

(22) Filed: Aug. 5, 2022

(65) Prior Publication Data

US 2023/0080821 A1    Mar. 16, 2023

(30) Foreign Application Priority Data

Sep. 10, 2021   (TW) ................ 110133826

(51) Int. Cl.
*G06K 9/00*   (2022.01)
*A61B 5/02*   (2006.01)
(Continued)

(52) U.S. Cl.
CPC .......... *A61B 5/02007* (2013.01); *A61B 5/055* (2013.01); *G06T 7/0012* (2013.01);
(Continued)

(58) Field of Classification Search
CPC ... A61B 5/02007; A61B 5/055; G06T 7/0012; G06T 7/10; G06T 2207/10088;
(Continued)

(56) References Cited

U.S. PATENT DOCUMENTS

2022/0399117 A1*  12/2022  Leuthardt ............. G06N 3/045

OTHER PUBLICATIONS

Cerebral amyloid burden is associated with white matter hypertensity location in specific posterior white matter regions, Nick A. Weaver et al., Elsevier, 2019, pp. 225-234 (Year: 2019).*

(Continued)

*Primary Examiner* — Jayesh A Patel
(74) *Attorney, Agent, or Firm* — Chih Feng Yeh; Yongjean Consulting Inc.

(57) ABSTRACT

A neurovascular age prediction system based on white matter and a method thereof are disclosed. An analysis device generates an individual space periventricular area mask and an individual space deep white matter mask by nonlinear space counterpoint technology and MNI152 brain template, and reversely transforms individual coordinates into a transition matrix, performs white matter hyperintensity (WMH) signal image processing on the T1 weighted image and the T2 fluid attenuated inversion recovery (FLAIR) image to generate a T1 weighted WMH signal image and a T2 FLAIR WMH signal image, then converts the Ti WMH signal image and the T2 FLAIR WMH signal image into logarithms of a periventricular white matter volume and a deep WMH volume based on the individual space periventricular area mask and the individual space deep white matter mask, and substitutes the logarithms into a neurovascular age prediction model to obtain a neurovascular age prediction result.

4 Claims, 6 Drawing Sheets

(51) Int. Cl.
*A61B 5/055* (2006.01)
*G06T 7/00* (2017.01)
*G06T 7/10* (2017.01)

(52) U.S. Cl.
CPC ...... *G06T 7/10* (2017.01); *G06T 2207/10088* (2013.01); *G06T 2207/30016* (2013.01); *G06T 2207/30096* (2013.01); *G06T 2207/30101* (2013.01)

(58) Field of Classification Search
CPC . G06T 2207/30016; G06T 2207/30096; G06T 2207/30101
See application file for complete search history.

(56) References Cited

OTHER PUBLICATIONS

Tract-defined regional white matter hyperintensities and memory, Batool Rizvi et al., Elsevier, 2019, pp. 1-7 (Year: 2019).*
White Matter Hyperintensities on 1.5 and 3 Tesla Brain MRI in Healthy Individuals, Carol Di Perri et al., Sciedu Press, 2013, pp. 53-62 (Year: 2013).*
Quantitative susceptibility mapping as a biomarker for evaluating white matter alterations in Parkinson's disease, Xiaojun Guan et al., Springer, 2018, pp. 220-231 (Year: 2018).*

* cited by examiner

NEUROVASCULAR AGE PREDICTION SYSTEM BASED ON WHITE MATTER HYPERINTENSITY SIGNAL AND METHOD THEREOF

CROSS-REFERENCE STATEMENT

The present application is based on, and claims priority from, Taiwan Patent Application Serial Number 110133826, filed Sep. 10, 2021, the disclosure of which is hereby incorporated by reference herein in its entirety.

BACKGROUND

1. Technical Field

The present invention is related to a prediction system and a method thereof, more particularly to a neurovascular age prediction system based on a white matter hyperintensity signal, and a method thereof.

2. Related Art

White matter hyperintensity (WMH) signal is the extremely high brightness signal observed in the white matter of the T2-weighted fluid attenuated inversion recovery (T2-FLAIR) image in magnetic resonance imaging data. The WMH signal is the main basis for clinical interpretation.

The reasons for the generation of the white matter hyperintensity signal are complex; in the absence of brain injury and special neurological diseases, it is generally believed that the generation of the white matter hyperintensity signal is mainly related to white matter nerve cell damage caused by transient ischemia, decreased cardiovascular function or chronic microvascular disease, and it is the brain representation of normal human aging during the aging process.

Recent studies have shown that the volume of white matter damaged part is significantly associated with cognitive decline, but the causes of damage in different brain parts and the affected cognitive abilities are not the same. The area, size and volume of the white matter injury are often very different in different cases, and it causes the complexity of the traditional clinical interpretation mechanism. However, in order to clearly describe the location of the injury, the workload of interpretation increases; in addition, the description is also easily affected by the experience and background of the diagnosing doctor, and different interpretations may cause the subject to ignore the timing of early diagnosis.

According to above-mentioned contents, what is needed is to develop an improved solution to solve the conventional problem that it is difficult to perform the clinical interpretation based on the white matter hyperintensity signal.

SUMMARY

An objective of the present invention is to disclose a neurovascular age prediction system based on white matter and a method thereof, to solve the conventional problem that it is difficult to perform the clinical interpretation based on the white matter hyperintensity signal.

In order to achieve the objective, the present invention provides a neurovascular age prediction system based on white matter, the neurovascular age prediction system includes a magnetic resonance device and an analysis device; the analysis device includes a receiving module, a transformation module, an atlas generation module, a mask generation module, an image processing module, an image calculation module, a value conversion module and a neurovascular age prediction module.

The magnetic resonance device is configured to detect a subject to generate magnetic resonance images, wherein the magnetic resonance images comprises a T1 weighted image and a T2 fluid attenuated inversion recovery (FLAIR) image.

The receiving module of the analysis device is configured to receive the magnetic resonance images from the magnetic resonance device. The transformation module of the analysis device is configured to transform the individual coordinates of T1 weighted image into the international standard coordinates by nonlinear space counterpoint technology, to generate a T1 weighted coordinate transformation image. The atlas generation module of the analysis device is configured to generate a ventricle mask based on a MNI152 international standard brain template, and extend the ventricle mask is outwardly by a preset distance to cover the T1 weighted coordinate transformation image, to generate a periventricular white matter atlas and a deep white matter atlas. The mask generation module of the analysis device is configured to reversely transform the individual coordinates to a transition matrix of international standard coordinate, and apply the transition matrix of international standard coordinate into the periventricular white matter atlas and the deep white matter atlas, to generate an individual space periventricular area mask and an individual space deep white matter mask, respectively. The image processing module of the analysis device is configured to perform white matter hyperintensity signal image processing on the T1 weighted image and the T2 fluid attenuated inversion recovery image, to generate a T1 weighted white matter hyperintensity signal image and a T2 fluid attenuated inversion recovery white matter hyperintensity signal image. The image calculation module of the analysis device is configured to use the individual space periventricular area mask and the individual space deep white matter mask to perform calculation on the T1 weighted white matter hyperintensity signal image and the T2 fluid attenuated inversion recovery white matter hyperintensity signal image to obtain a periventricular white matter hyperintensity volume and a deep white matter hyperintensity volume, respectively. The value conversion module of the analysis device is configured to perform logarithm conversion on the periventricular white matter hyperintensity volume and the deep white matter hyperintensity volume, to generate a logarithm of periventricular white matter hyperintensity volume and a logarithm of the deep white matter hyperintensity volume value. The neurovascular age prediction module of the analysis device is configured to substitute the logarithm of periventricular white matter hyperintensity volume and the logarithm of the deep white matter hyperintensity volume into a neurovascular age prediction model, to obtain a neurovascular age prediction result.

In order to achieve the objective, the present invention provides a neurovascular age prediction method based on white matter, and the neurovascular age prediction method includes steps of performing a brain scan on a subject to generate magnetic resonance images, by a magnetic resonance device, wherein the magnetic resonance images include a T1 weighted image and a T2 fluid attenuated inversion recovery image; receiving the magnetic resonance images from the magnetic resonance device, by an analysis device; transforming the individual coordinates of the T1 weighted image into international standard coordinates through a nonlinear space counterpoint technology, to generate a T1 weighted coordinate transformation image, by the analysis device; generating a ventricle mask based on a MNI152 international standard brain template, extending the ventricle mask outwardly by a preset distance to cover the T1 weighted coordinate transformation image to generate a periventricular white matter atlas and a deep white matter atlas, by the analysis device; reversely transforming the individual coordinate into a transition matrix of international standard coordinate, and applying the transition matrix of international standard coordinate to the periventricular white matter atlas and the deep white matter atlas to generate an individual space periventricular area mask and an individual space deep white matter mask, respectively, by the analysis device; performing a white matter hyperintensity signal image processing on the T1 weighted image and the T2 fluid attenuated inversion recovery image to generate a T1 weighted white matter hyperintensity signal image and a T2 fluid attenuated inversion recovery white matter hyperintensity signal image, by the analysis device; using the individual space periventricular area mask and the individual space deep white matter mask to perform calculation on the T1 weighted white matter hyperintensity signal image and the T2 fluid attenuated inversion recovery white matter hyperintensity signal image, to obtain a periventricular white matter hyperintensity volume and a deep white matter hyperintensity volume, respectively, by the analysis device; performing logarithm conversion on the periventricular white matter hyperintensity volume and the deep white matter hyperintensity volume to generate a logarithm of the periventricular white matter hyperintensity volume and a logarithm of the deep white matter hyperintensity volume value, by the analysis device; substituting the logarithm of periventricular white matter hyperintensity volume and the logarithm of the deep white matter hyperintensity volume into a neurovascular age prediction model to obtain a neurovascular age prediction result, by the analysis device.

According to the above-mentioned system and method of the present invention, the difference between the present invention and the conventional technology is that, in the present invention, the analysis device generates the individual space periventricular area mask and the individual space deep white matter mask by the nonlinear space counterpoint technology and MNI152 international standard brain template, and reversely transforms individual coordinates into the transition matrix of international standard coordinate, performs the white matter hyperintensity signal image processing on the T1 weighted image and the T2 fluid attenuated inversion recovery image to generate a T1 weighted white matter hyperintensity signal image and a T2 fluid attenuated inversion recovery white matter hyperintensity signal image; the analysis device then performs logarithm conversion on the T1 weighted white matter hyperintensity signal image and the T2 fluid attenuated inversion recovery white matter hyperintensity signal image to generate the logarithm of the periventricular white matter volume and the logarithm of the deep white matter hyperintensity volume based on the individual space periventricular area mask and the individual space deep white matter mask, respectively, and substitutes the logarithm of the periventricular white matter volume and the logarithm of the deep white matter hyperintensity volume into the neurovascular age prediction model to obtain the neurovascular age prediction result.

Therefore, the above-mentioned technical solution of the present invention is able to achieve the technical effect of providing neurovascular age prediction based on the white matter hyperintensity signal and evaluating odds ratio.

BRIEF DESCRIPTION OF THE DRAWINGS

The structure, operating principle and effects of the present invention will be described in detail by way of various embodiments which are illustrated in the accompanying drawings.

DETAILED DESCRIPTION

Figure 1:
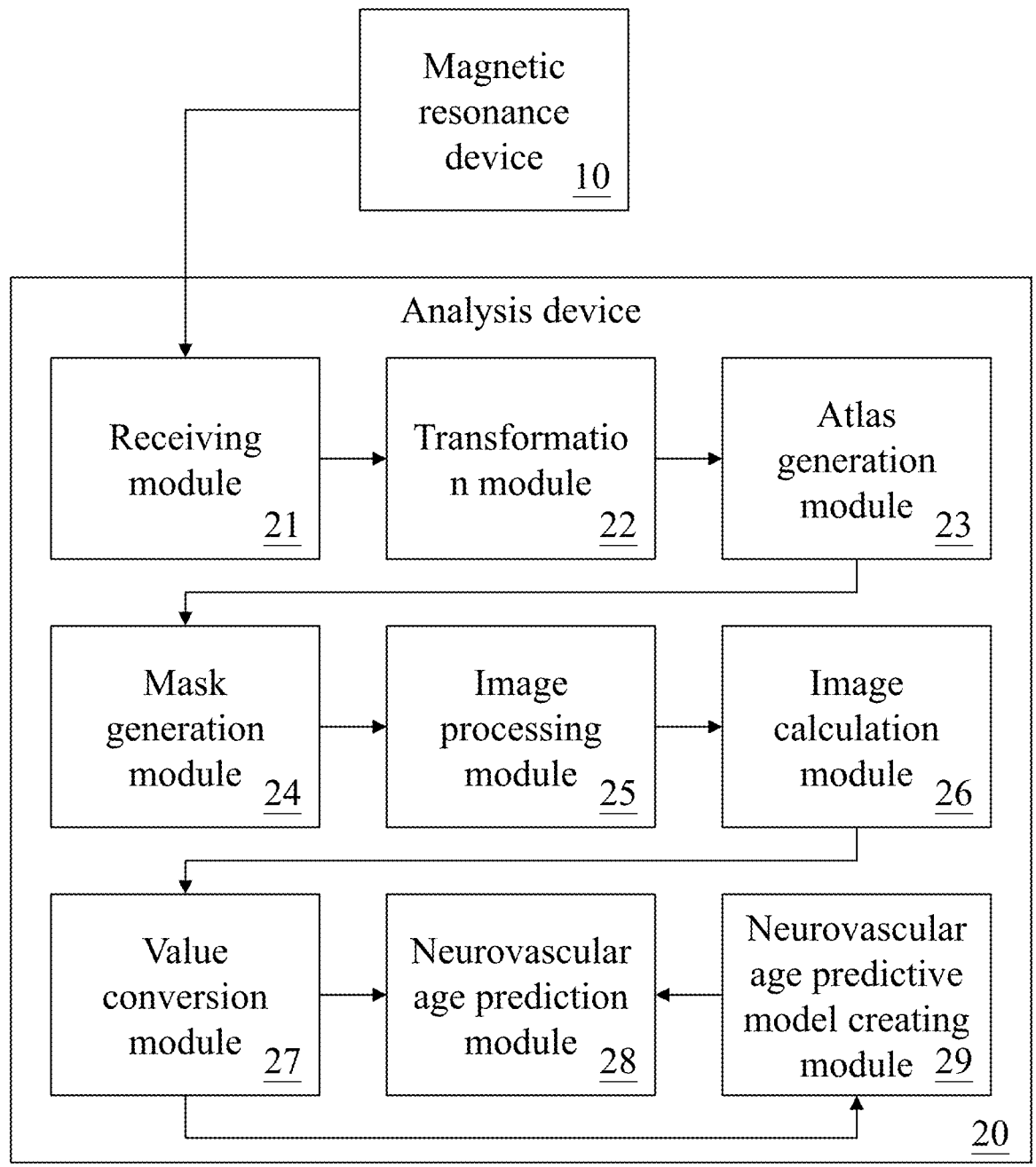
FIG. 1 is a system block diagram of a neurovascular age prediction system based on white matter, according to the present invention.

The following embodiments of the present invention are herein described in detail with reference to the accompanying drawings. These drawings show specific examples of the embodiments of the present invention. These embodiments are provided so that this disclosure will be thorough and complete, and will fully convey the scope of the invention to those skilled in the art. It is to be acknowledged that these embodiments are exemplary implementations and are not to be construed as limiting the scope of the present invention in any way. Further modifications to the disclosed embodiments, as well as other embodiments, are also included within the scope of the appended claims.

These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts. As used herein, the singular forms "a", "an" and "the" are intended to include the plural forms as well, unless the context clearly indicates otherwise. As used herein, the term "or" includes any and all combinations of one or more of the associated listed items.

It will be acknowledged that when an element or layer is referred to as being "on," "connected to" or "coupled to" another element or layer, it can be directly on, connected or coupled to the other element or layer, or intervening elements or layers may be present. In contrast, when an element is referred to as being "directly on," "directly connected to" or "directly coupled to" another element or layer, there are no intervening elements or layers present.

In addition, unless explicitly described to the contrary, the words "comprise" and "include", and variations such as "comprises", "comprising", "includes", or "including", will be acknowledged to imply the inclusion of stated elements but not the exclusion of any other elements.

The neurovascular age prediction system of the present invention will be described in the following paragraphs. Please refer to FIG. 1, which is a system block diagram of a neurovascular age prediction system based on white matter, according to the present invention.

The neurovascular age prediction system includes a magnetic resonance device 10 and an analysis device 20; the analysis device 20 includes a receiving module 21, a transformation module 22, an atlas generation module 23, a mask generation module 24, an image processing module 25, an image calculation module 26, a value conversion module 27 and a neurovascular age prediction module 28.

The magnetic resonance device 10 performs brain scan on a subject to generate magnetic resonance images. In an embodiment, the magnetic resonance images include a T1 weighted image and a T2 fluid attenuated inversion recovery image.

The analysis device 20 can be interconnected with the magnetic resonance device 10 through wired transmission manner or wireless transmission manner; for example, the wired transmission manner can be power line network or optical network, the wireless transmission manner can be Wi-Fi, mobile communication network (such as 4G, or 5G), these examples are merely for exemplary illustration, but, the application field of the present invention is not limited to these examples.

The receiving module 21 of the analysis device 20 receives the magnetic resonance images from the magnetic resonance device 10, the transformation module 22 of the analysis device 20 transforms the individual coordinates of T1 weighted image into international standard coordinates by nonlinear space counterpoint technology, to generate a T1 weighted coordinate transformation image.

The atlas generation module 23 of the analysis device 20 generates a ventricle mask based on the Montreal Neurological Institute (MNI) 152 international standard brain template, and extends the ventricle mask outwardly by a preset distance to cover the T1-weighted coordinate transformation image, to generate a periventricular white matter atlas and a deep white matter atlas; for example, the preset distance can be 10 mm, but it is merely for exemplary illustration, and the application field of the present invention is not limited to these examples. Particularly, the ventricle mask is extended outwardly by the preset distance to cover the T1 weighted coordinate transformation image, the part within the preset distance can be used to generate the periventricular white matter atlas, and the part outside the preset distance can be used to generate the deep white matter atlas.

The mask generation module 24 of the analysis device 20 reversely transforms the individual coordinates into a transition matrix of international standard coordinate, and applies the transition matrix of international standard coordinate into the periventricular white matter atlas and the deep white matter atlas, to generate an individual space periventricular area mask and an individual space deep white matter mask, respectively.

The image processing module 25 of the analysis device 20 performs a white matter hyperintensity signal image processing on the T1 weighted image and the T2 fluid attenuated inversion recovery image, to generate a T1 weighted white matter hyperintensity signal image and a T2 fluid attenuated inversion recovery white matter hyperintensity signal image. The image processing module 25 of the analysis device 20 performs the white matter hyperintensity signal image processing on the T1 weighted image and the T2 fluid attenuated inversion recovery image by lesion segmentation technology to obtain the spatial position of an abnormal white matter hyperintensity signal, and then performs image processing on the T1 weighted image and the T2 fluid attenuated inversion recovery image to generate the T1 weighted white matter hyperintensity signal image and the T2 fluid attenuated inversion recovery white matter hyperintensity signal image.

The image calculation module 26 of the analysis device 20 uses the individual space periventricular area mask and the individual space deep white matter mask to calculate the T1 weighted white matter hyperintensity image and the T2 fluid attenuated inversion recovery white matter hyperintensity image, respectively, so as to obtain a periventricular white matter hyperintensity volume and a deep white matter hyperintensity volume.

The value conversion module 27 of the analysis device 20 performs logarithm conversion on the periventricular white matter hyperintensity volume and the deep white matter hyperintensity volume, to obtain a logarithm of the periventricular white matter hyperintensity volume and a logarithm of the deep white matter hyperintensity volume value.

The neurovascular age prediction module 28 of the analysis device 20 substitutes the logarithm of periventricular white matter volume and the logarithm of the deep white matter hyperintensity volume into the neurovascular age prediction model, to obtain a neurovascular age prediction result. Particularly, the neurovascular age prediction model can be, for example, $a*\log_{10}(PVWMH)+b+\log_{10}(DWMH)+c$, wherein a is 11.069, b is 1.624, c is 64.159, PVWMH is the logarithm of periventricular white matter volume value, DWMH is the logarithm of the deep white matter hyperintensity volume value; in actual data, in a condition that the chronological age is 62.6, the calculated PVWMH is 1.12 and the calculated DWMH is 0.19, the neurovascular age prediction result is 63.86 ($63.86=11.069*\log_{10}(1.12)+1.624*\log_{10}(0.19)+64.159$); in a condition that the chronological age is 69.4, the calculated PVWMH is 10.55 and the calculated DWMH is 0.50, the neurovascular age prediction result is 74.99 ($74.99=11.069*\log_{10}(10.55)+1.624*\log_{10}(0.5)+64.159$; in a condition that the chronological age is 80.6, the calculated PVWMH is 12.95, the calculated DWMH is 1.89, the neurovascular age prediction result is 76.78 ($76.78=11.069*\log_{10}(12.95)+1.624*\log_{10}(1.89)+63.597$; however, these examples are merely for exemplary illustration, and the application field of the present invention is not limited to these examples.

In order to create the neurovascular age prediction model, the magnetic resonance device 10 performs the brain scan on multiple health subjects to generate multiple health magnetic resonance images, the magnetic resonance images include the T1 weighted images and the T2 fluid attenuated inversion recovery images.

The receiving module 21 of the analysis device 20 receives the health magnetic resonance images from the magnetic resonance device 10, the transformation module 22 of the analysis device 20 transforms the individual coordinates of T1 weighted images into international standard coordinates by the nonlinear space counterpoint technology, to generate T1 weighted coordinate transformation images.

The atlas generation module 23 of the analysis device 20 generates a ventricle mask based on the MNI152 international standard brain template and extends the ventricle mask outwardly by a preset distance (such as 10 mm, but this example is merely for exemplary illustration, and the application field of the present invention is not limited to the example) to cover each T1 weighted coordinate transformation image, to generate periventricular white matter atlases and deep white matter atlases.

The mask generation module 24 of the analysis device 20 reversely transforms the individual coordinates into the transition matrix of international standard coordinates, and applies the transition matrix of international standard coordinates into each of the periventricular white matter atlas and each of the deep white matter atlas, to generate individual space periventricular area masks and individual space deep white matter masks, respectively.

The image processing module 25 of the analysis device 20 performs white matter hyperintensity signal image processing on the each of the T1 weighted images and each of the T2 fluid attenuated inversion recovery images, to generate T1 weighted white matter hyperintensity signal images and T2 fluid attenuated inversion recovery white matter hyperintensity signal images.

The image calculation module 26 of the analysis device 20 uses the individual space periventricular area masks and the individual space deep white matter masks to calculation on the T1 weighted white matter hyperintensity signal images and the T2 fluid attenuated inversion recovery white matter hyperintensity signal images, respectively, to obtain the periventricular white matter hyperintensity volumes and the deep white matter hyperintensity volumes.

The value conversion module 27 of the analysis device 20 performs the logarithm conversion on the each of the periventricular white matter hyperintensity volume and the each of the deep white matter hyperintensity volume, to obtain the logarithms of periventricular white matter hyperintensity volumes and logarithms of the deep white matter hyperintensity volumes.

Figure 2:
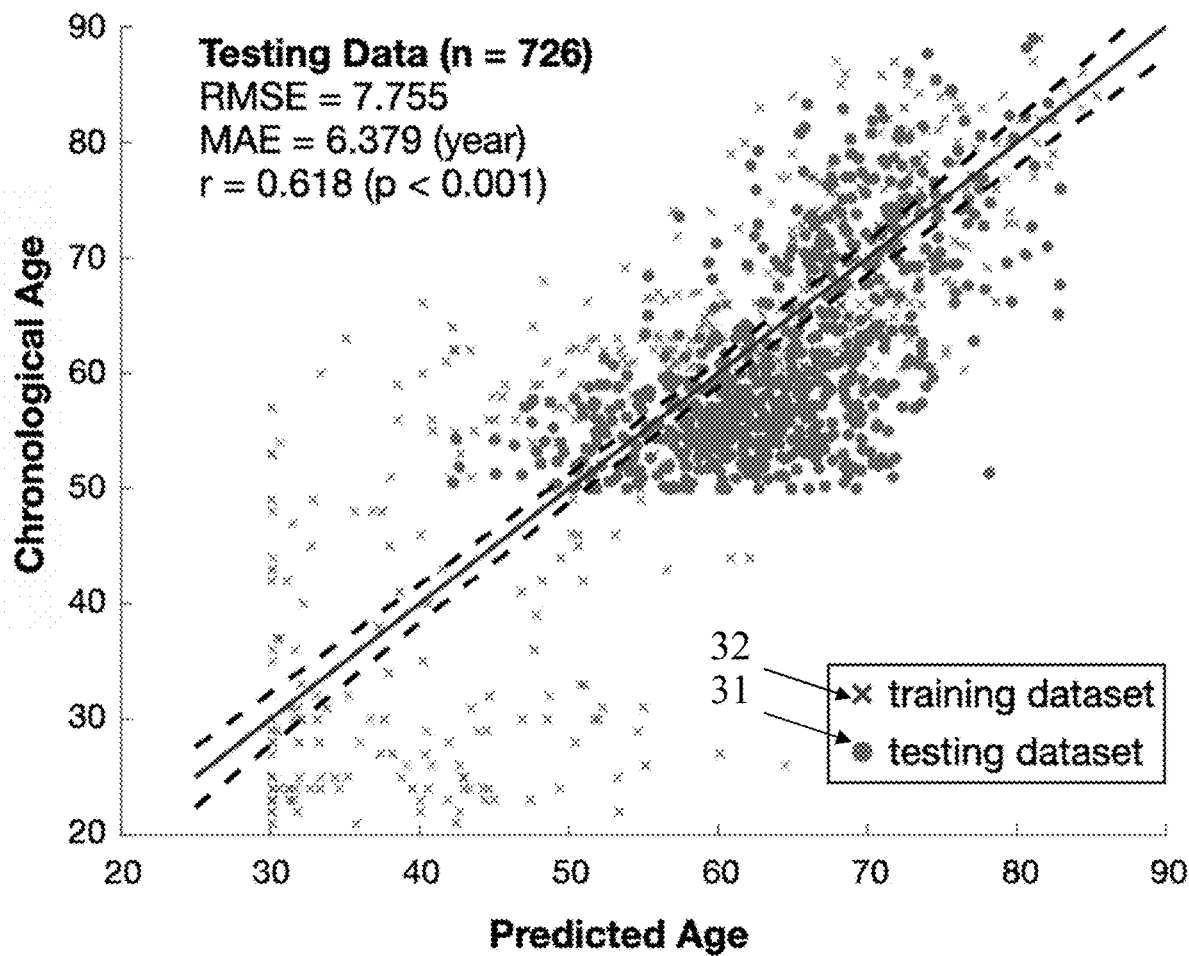
FIG. 2 is a diagram showing data for creating a neurovascular age prediction model based on white matter, according to the present invention.

The neurovascular age predictive model creating module 29 of the analysis device 20 creates the neurovascular age prediction model by the hold-out validation and the 10-fold cross-validation, and randomly selects the preset percentage amount (such as 30%, but this example is merely for exemplary illustration, and the application field of the present invention is not limited to the example) of the logarithms of periventricular white matter hyperintensity volumes and the logarithm of the deep white matter hyperintensity volumes, as the testing dataset 31, and uses the logarithms of the deep white matter hyperintensity volumes not being selected as the training dataset 32 to perform linear regression, and then performs stability validation on the result of linear regression by the 10-fold cross-validation; that is, RMSE, MAE, R2 and AIC of different results of linear regression are compared, for example, smaller RMSE, MAE and AIC and higher R-squared indicate the better result of linear regression, so that the relatively stable result of linear regression can be found as the neurovascular age prediction model. Next, the testing dataset is substituted into the neurovascular age prediction model to perform the model universality validation. Please refer to FIG. 2, which is a diagram showing data for creating a neurovascular age prediction model based on white matter, according to the present invention. As shown in FIG. 2, the data points of the testing dataset 31 are marked with solid circles, the data points of the training dataset 32 are marked with X; however, these examples are merely for exemplary illustration, and the application field of the present invention is not limited to these examples.

Figure 3A:
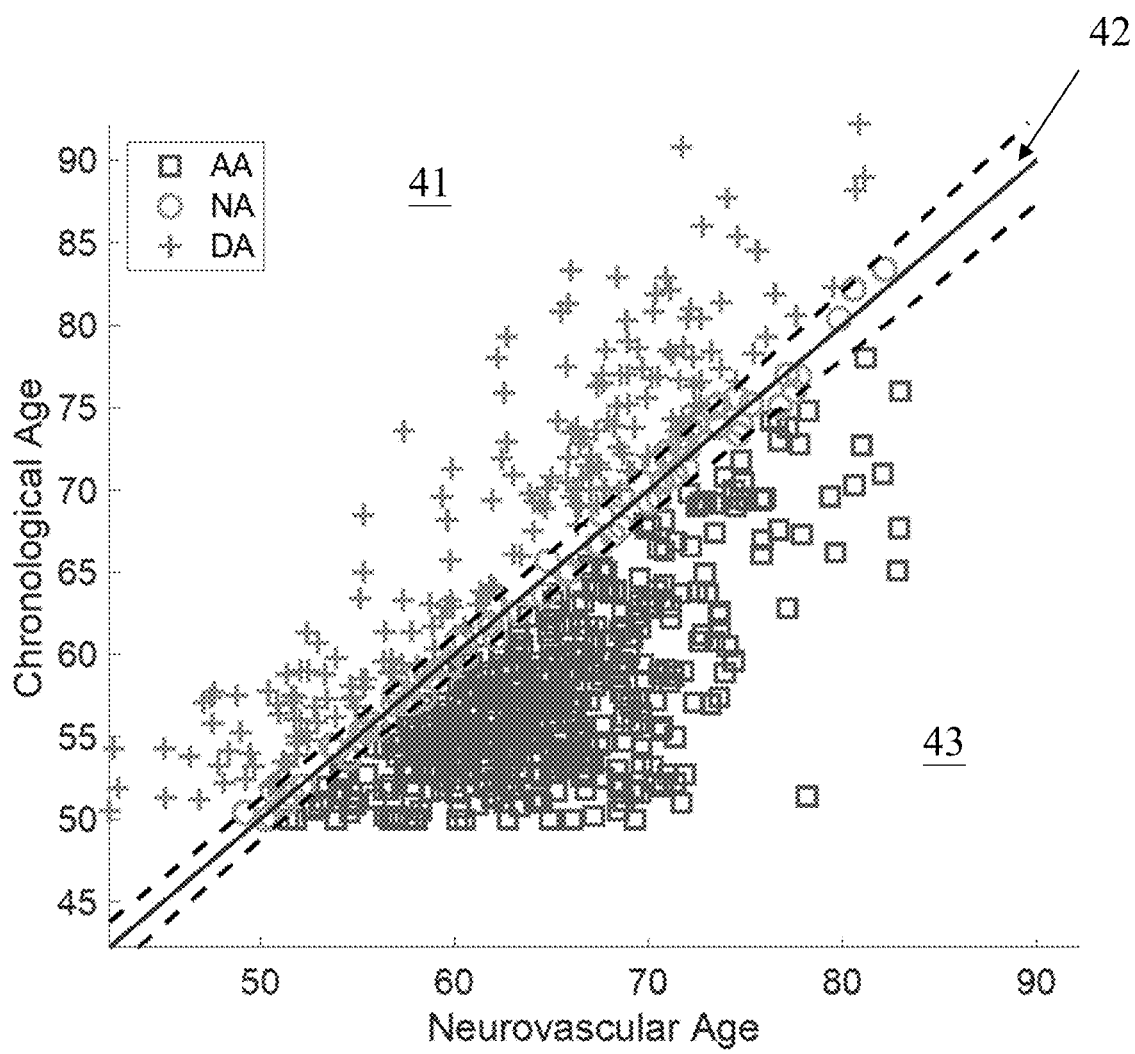
FIG. 3A is a diagram showing chronological ages and ages predicted by a neurovascular age prediction system based on white matter, according to the present invention.
Figure 3B:
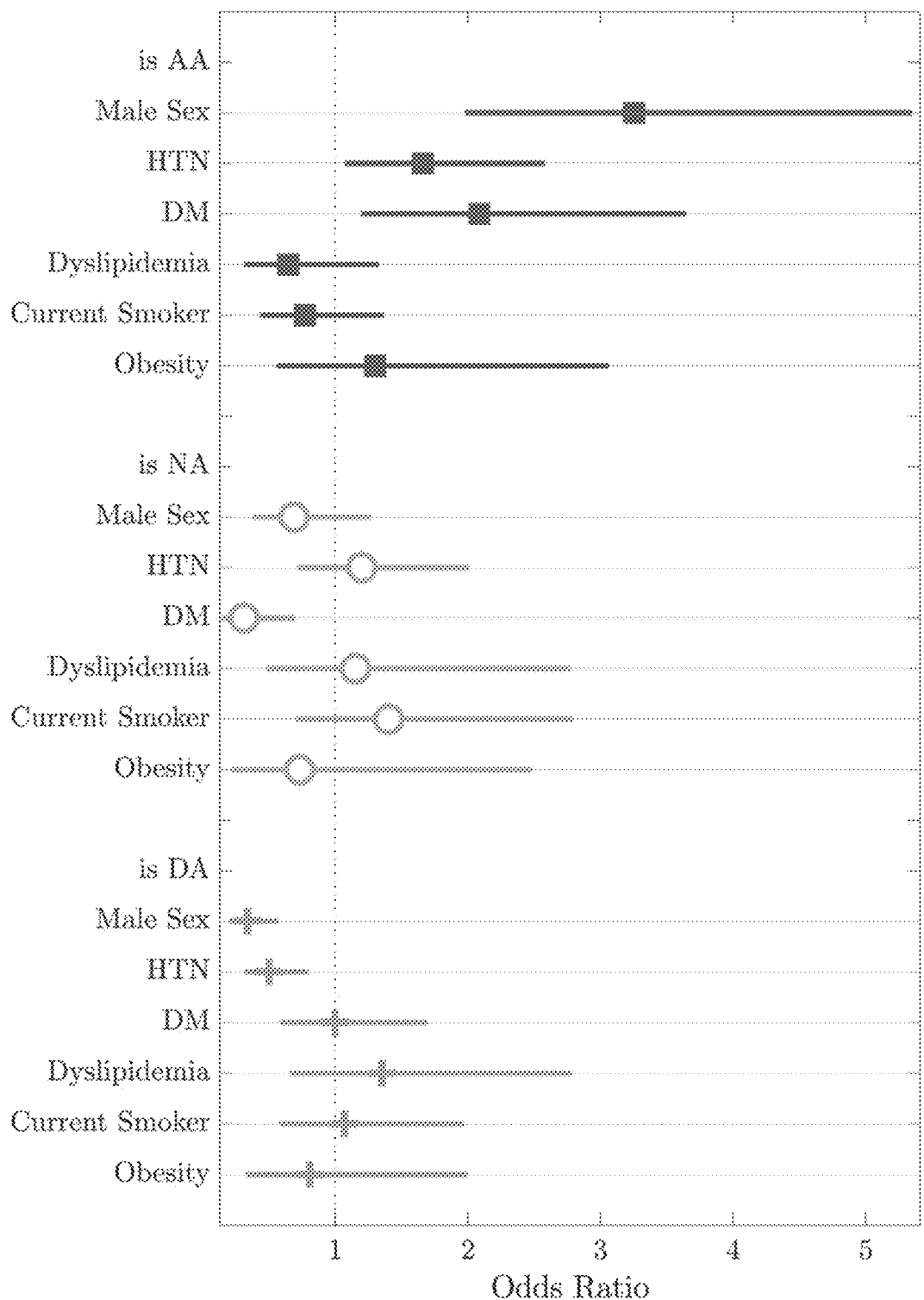
FIG. 3B is a diagram showing comparison analysis of cardiovascular risk indicators of neurovascular age prediction based on white matter, according to the present invention.

Please refer to FIGS. 3A and 3B. FIG. 3A is a diagram showing chronological ages and ages predicted by a neurovascular age prediction system based on white matter, according to the present invention. FIG. 3B is a diagram showing comparison analysis of cardiovascular risk indicators of neurovascular age prediction based on white matter, according to the present invention.

As shown in FIG. 3A, the area where the neurovascular age prediction values are lower than the chronological ages, that is, the area above an upper boundary of 95% confidence interval, is defined as a delayed aging area 41; the area where the neurovascular age prediction values are equivalent to the chronological ages is defined as a normal aging area 42, and the area where the neurovascular age prediction values are higher than the chronological age is defined as an accelerated aging area 43.

FIG. 3B shows an odds ratio analysis of common clinical cardiovascular risk indicators and the delayed aging area 41, the normal aging area 42 and the accelerated aging area 43 of FIG. 3A. As shown in the comparison analysis in FIG. 3B, the risk of male being classified as the accelerated aging area 43 is higher than that of female, the ratio is 2.5 (such as, in a range of 1.8 to 3.47), the aging rate of hypertension (HTN) classified into the accelerated aging area 43 is 2.492 (such as, in a range of 1.744 to 3.561), the aging rate of diabetes (DM) classified into the accelerated aging area 43 is 2.67 (such as, in a range of 1.68 to 4.23); other indicators, such as dyslipidemia, smoking and obesity, do not significantly accelerate the risk of brain neurovascular aging, so cardiovascular risk factors (such as male, HTN, and DM, but these examples are merely for exemplary illustration, and the application field of the present invention is not limited to these examples) cause increase of white matter damage, and make the predicted cerebral neurovascular age relatively high.

The analysis architecture and created neurovascular age prediction model of the present invention is able to predict individual brain age based on volume of the damaged white matter, to facilitate clinical promotion; the quantitative index can be applied to the aging rate assessment and to neurodegenerative diseases caused by cardiovascular diseases, so as to provide medical personnel with an objective quantitative index to assist in diagnosis and to assist doctors in assessing physical examination of a health person or determining the possible causes of white matter degeneration or damage in clinical patients, thereby giving recommendations related to cardiovascular risk factors.

The operation of the present invention will be described in the following paragraphs. Please refer to FIGS. 4A and 4B, which are flowcharts of a neurovascular age prediction method based on white matter, according to the present invention.

Figure 4A:
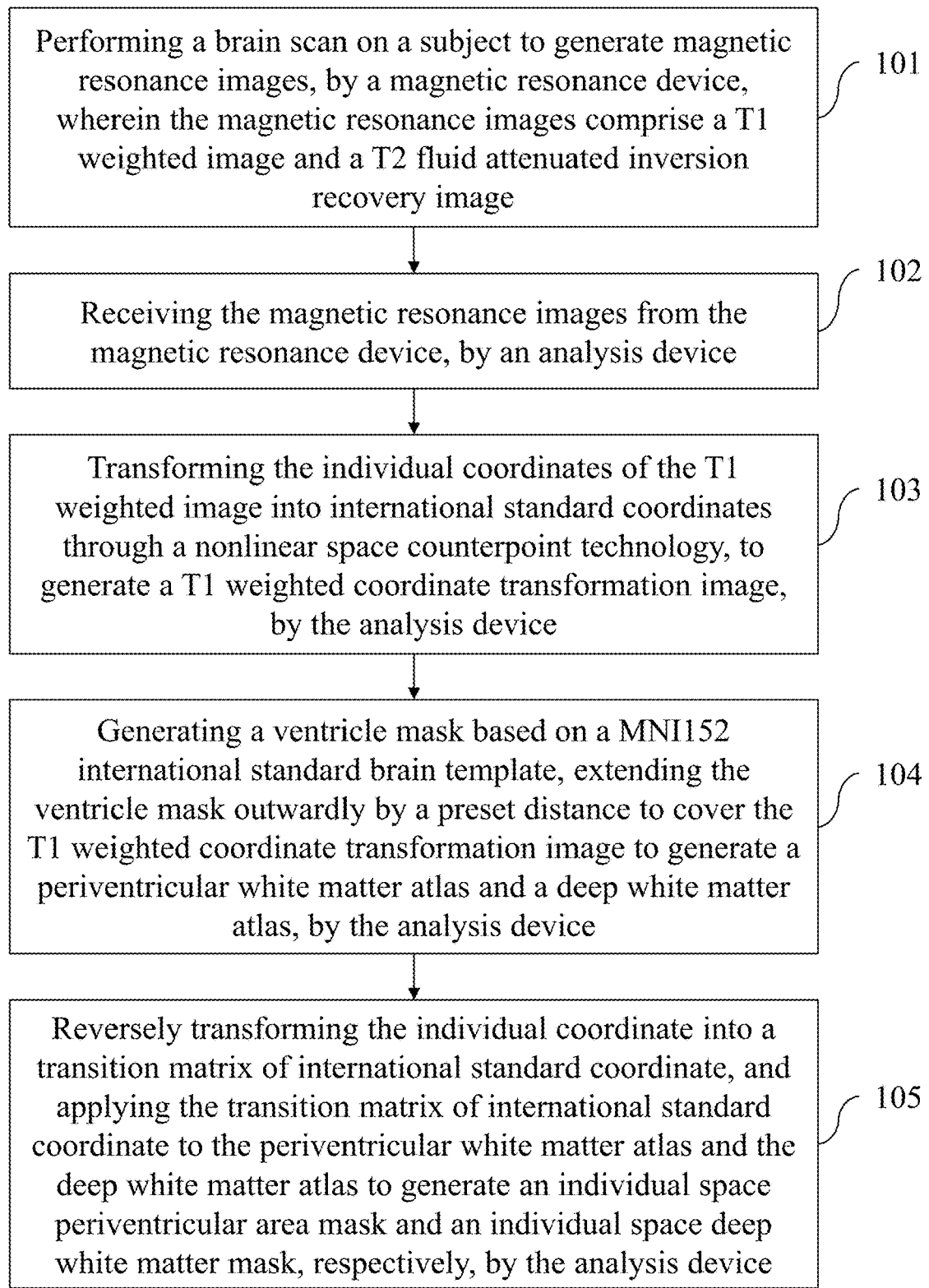
FIGS. 4A and 4B are flowcharts of a neurovascular age prediction method based on white matter, according to the present invention.
Figure 4B:
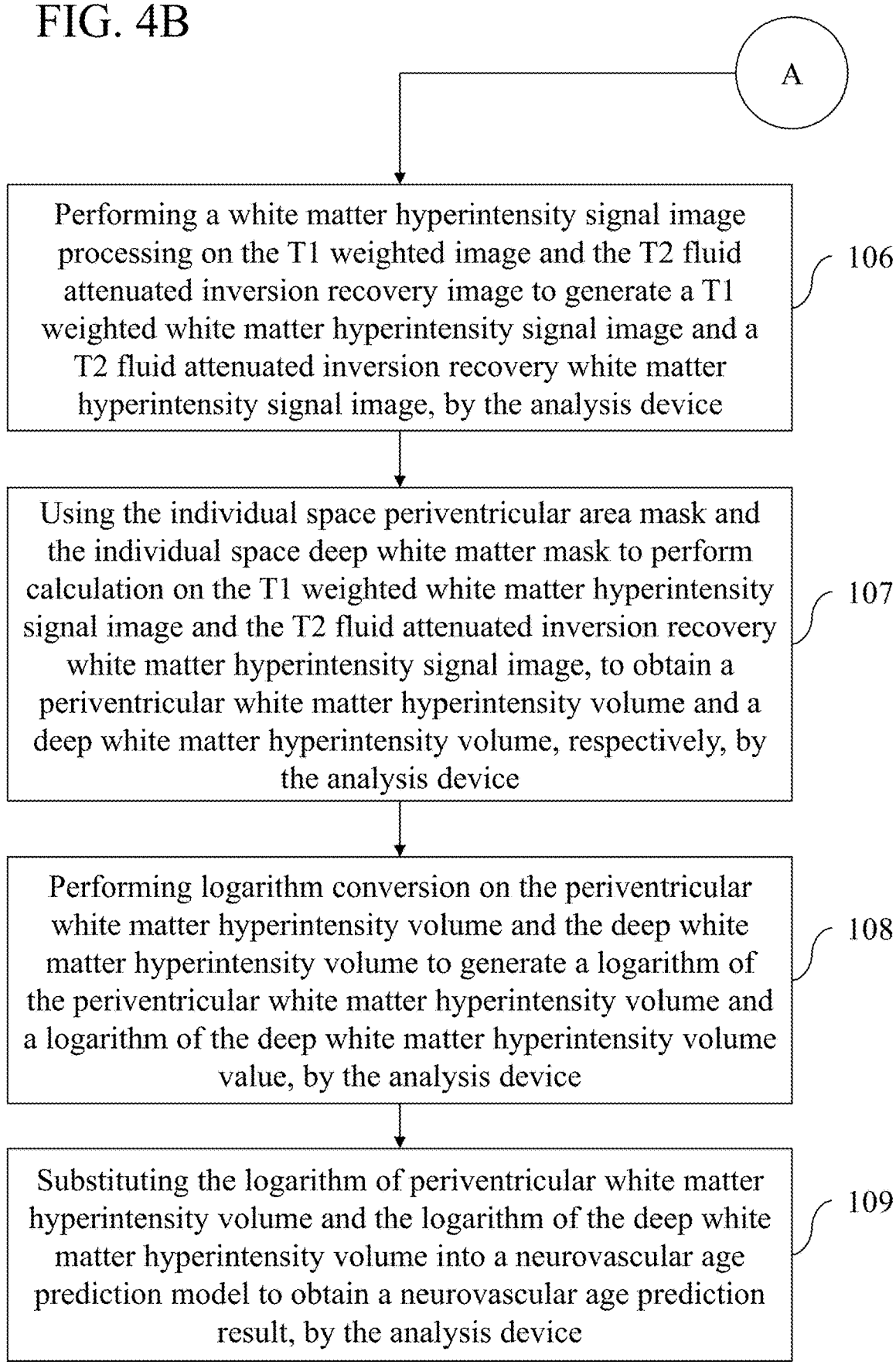

As shown in FIGS. 4A and 4B, in a step 101, a magnetic resonance device performs a brain scan on a subject to generate magnetic resonance images, wherein the magnetic resonance images include a T1 weighted image and a T2 fluid attenuated inversion recovery image. In a step 102, an analysis device receives the magnetic resonance images from the magnetic resonance device. In a step 103, the analysis device transforms the individual coordinates of the T1 weighted image into international standard coordinates through a nonlinear space counterpoint technology, to generate a T1 weighted coordinate transformation image. In a step 104, the analysis device generates a ventricle mask based on a MNI152 international standard brain template, and extends the ventricle mask outwardly by a preset distance to cover the T1 weighted coordinate transformation image to generate a periventricular white matter atlas and a deep white matter atlas. In a step 105, the analysis device reversely transforms the individual coordinate into a transition matrix of international standard coordinate, and applies the transition matrix of international standard coordinate to the periventricular white matter atlas and the deep white matter atlas to generate an individual space periventricular area mask and an individual space deep white matter mask, respectively. In a step 106, the analysis device performs a white matter hyperintensity signal image processing on the T1 weighted image and the T2 fluid attenuated inversion recovery image to generate a T1 weighted white matter hyperintensity signal image and a T2 fluid attenuated inversion recovery white matter hyperintensity signal image. In a step 107, the analysis device uses the individual space periventricular area mask and the individual space deep white matter mask to perform calculation on the T1 weighted white matter hyperintensity signal image and the T2 fluid attenuated inversion recovery white matter hyperintensity signal image, to obtain a periventricular white matter hyperintensity volume and a deep white matter hyperintensity volume, respectively. In a step 108, the analysis device performs logarithm conversion on the periventricular white matter hyperintensity volume and the deep white matter hyperintensity volume to generate a logarithm of the periventricular white matter hyperintensity volume and a logarithm of the deep white matter hyperintensity volume value. In a step 109, the analysis device substitutes the logarithm of periventricular white matter hyperintensity volume and the logarithm of the deep white matter hyperintensity volume into a neurovascular age prediction model to obtain a neurovascular age prediction result.

According to above-mentioned contents, the difference between the present invention and the conventional technology, in the present invention, the analysis device generates the individual space periventricular area mask and the individual space deep white matter mask by the nonlinear space counterpoint technology and MNI152 international standard brain template, and reversely transforms individual coordinates into the transition matrix of international standard coordinate, performs the white matter hyperintensity signal image processing on the T1 weighted image and the T2 fluid attenuated inversion recovery image to generate a T1 weighted white matter hyperintensity signal image and a T2 fluid attenuated inversion recovery white matter hyperintensity signal image; the analysis device then performs logarithm conversion on the T1 weighted white matter hyperintensity signal image and the T2 fluid attenuated inversion recovery white matter hyperintensity signal image to generate the logarithm of the periventricular white matter volume and the logarithm of the deep white matter hyperintensity volume based on the individual space periventricular area mask and the individual space deep white matter mask, respectively, and substitutes the logarithm of the periventricular white matter volume and the logarithm of the deep white matter hyperintensity volume into the neurovascular age prediction model to obtain the neurovascular age prediction result.

Therefore, the above-mentioned technical solution of the present invention is able to solve the conventional problem that it is difficult to perform the clinical interpretation based on the white matter hyperintensity signal, to achieve the technical effect of providing neurovascular age prediction based on the white matter hyperintensity signal and evaluating odds ratio.

The present invention disclosed herein has been described by means of specific embodiments. However, numerous modifications, variations and enhancements can be made thereto by those skilled in the art without departing from the spirit and scope of the disclosure set forth in the claims.

What is claimed is:

1. A neurovascular age prediction method based on white matter, comprising:
    performing a brain scan on a subject to generate magnetic resonance images, by a magnetic resonance device, wherein the magnetic resonance images comprise a T1 weighted image and a T2 fluid attenuated inversion recovery image;
    receiving the magnetic resonance images from the magnetic resonance device, by an analysis device;
    transforming the individual coordinates of the T1 weighted image into international standard coordinates through a nonlinear space counterpoint technology, to generate a T1 weighted coordinate transformation image, by the analysis device;
    generating a ventricle mask based on a MNI152 international standard brain template, and extending the ventricle mask outwardly by a preset distance to cover the T1 weighted coordinate transformation image to generate a periventricular white matter atlas and a deep white matter atlas, by the analysis device;
    reversely transforming the individual coordinate into a transition matrix of international standard coordinate, and applying the transition matrix of international standard coordinate to the periventricular white matter atlas and the deep white matter atlas to generate an individual space periventricular area mask and an individual space deep white matter mask, respectively, by the analysis device;
    performing a white matter hyperintensity signal image processing on the T1 weighted image and the T2 fluid attenuated inversion recovery image to generate a T1 weighted white matter hyperintensity signal image and a T2 fluid attenuated inversion recovery white matter hyperintensity signal image, by the analysis device;
    using the individual space periventricular area mask and the individual space deep white matter mask to perform calculation on the T1 weighted white matter hyperintensity signal image and the T2 fluid attenuated inversion recovery white matter hyperintensity signal image, to obtain a periventricular white matter hyperintensity volume and a deep white matter hyperintensity volume, respectively, by the analysis device;
    performing logarithm conversion on the periventricular white matter hyperintensity volume and the deep white matter hyperintensity volume to generate a logarithm of the periventricular white matter hyperintensity volume and a logarithm of the deep white matter hyperintensity volume value, by the analysis device; and
    substituting the logarithm of periventricular white matter hyperintensity volume and the logarithm of the deep white matter hyperintensity volume into a neurovascular age prediction model to obtain a neurovascular age prediction result, by the analysis device.

2. The neurovascular age prediction method based on white matter according to claim 1, wherein the step of performing the white matter hyperintensity signal image processing on the T1 weighted image and the T2 fluid attenuated inversion recovery image to generate the T1 weighted white matter hyperintensity signal image and the T2 fluid attenuated inversion recovery white matter hyperintensity signal image, by the analysis device, comprises:
    obtaining a spatial position of abnormal white matter hyperintensity signal by using lesion segmentation technology, and performing the white matter hyperintensity signal image processing on the T1 weighted image and the T2 fluid attenuated inversion recovery image based on the spatial position.

3. The neurovascular age prediction method based on white matter according to claim 1, using hold-out validation and 10-fold cross-validation, to create the neurovascular age prediction model, by the analysis device.

4. The neurovascular age prediction method based on white matter according to claim 3, wherein the step of creating the neurovascular age prediction model by the hold-out validation and the 10-fold cross-validation, by the analysis device, comprises:
   randomly selecting a preset percentage of logarithms of periventricular white matter hyperintensity volume and logarithms of the deep white matter hyperintensity volume as a testing dataset;
   using the logarithms of the deep white matter hyperintensity volumes not being selected as a training dataset to perform linear regression, and performing stability validation on a result of the linear regression by 10-fold cross-validation to find the result of linear regression with high stability as the neurovascular age prediction model; and
   substituting the testing dataset into the neurovascular age prediction model to perform model universality validation.

\* \* \* \* \*